(12) United States Patent
Nosrati et al.

(10) Patent No.: US 10,852,298 B2
(45) Date of Patent: Dec. 1, 2020

(54) DEVICES AND METHODS FOR QUANTIFICATION OF MALE FERTILITY

(71) Applicant: THE GOVERNING COUNCIL OF THE UNIVERSITY OF TORONTO, Toronto (CA)

(72) Inventors: Reza Nosrati, Kingston (CA); Max M. Gong, Guelph (CA); David Sinton, Toronto (CA)

(73) Assignees: Reza Nosrati, Doncaster (AU); Max M. Gong, Fort Wayne, IN (US); David Stinton, Toronto (CA)

( * ) Notice: Subject to any disclaimer, the term of this patent is extended or adjusted under 35 U.S.C. 154(b) by 229 days.

(21) Appl. No.: 15/775,612

(22) PCT Filed: Nov. 18, 2016

(86) PCT No.: PCT/CA2016/051352
§ 371 (c)(1),
(2) Date: May 11, 2018

(87) PCT Pub. No.: WO2017/083981
PCT Pub. Date: May 26, 2017

(65) Prior Publication Data
US 2018/0348207 A1 Dec. 6, 2018

Related U.S. Application Data

(60) Provisional application No. 62/258,178, filed on Nov. 20, 2015.

(51) Int. Cl.
*G01N 33/50* (2006.01)
*B01L 3/00* (2006.01)
(Continued)

(52) U.S. Cl.
CPC ........ *G01N 33/5091* (2013.01); *B01L 3/5023* (2013.01); *C12N 5/061* (2013.01);
(Continued)

(58) Field of Classification Search
CPC .... G01N 33/5091; G01N 30/00; G01N 15/06; G01N 33/525; G01N 21/78;
(Continued)

(56) References Cited

U.S. PATENT DOCUMENTS 5,434,057 A 7/1995 Dorian
5,763,206 A * 6/1998 Hammerstedt .... G01N 33/5005
424/561

(Continued)

FOREIGN PATENT DOCUMENTS

CA 2931201 5/2015
WO 2010009307 1/2010
(Continued)

OTHER PUBLICATIONS

Brezina PR, Haberl E, Wallach E. At home testing: Optimizing management for the infertility physician. Fertil Steril. 2011;95:1867-78.
(Continued)

*Primary Examiner* — Benjamin R Whatley
*Assistant Examiner* — Jean Caraballo-Leon
(74) *Attorney, Agent, or Firm* — Hill & Schmacher

(57) ABSTRACT

Disclosed herein is a low cost and rapid microfluidic based method and test device for quantifying male fertility potential. The device can simultaneously measure three critical semen parameters rapidly, namely live sperm concentration, motile sperm concentration, and sperm motility. The device includes a transparent substrate and a top sheet with two holes therethrough and an intermediate sheet sandwiched between the substrate and the top sheet. The wells formed by
(Continued)

holes form a concentration measuring well (C) and a motility well (M) formed by the top sheet with these two holes bonded to the intermediate sheet. A colorimetric agent is located on the top surface of the intermediate sheet at the bottom of each well which changes color when in contact with sperm. In the motility well a porous membrane is located on top of the colorimetric agent and a liquid buffer may be placed on the top surface of the porous membrane. Applying part of a sperm sample to the C well results in direct contact of any live sperm with the colorimetric agent causing a color change, applying part of the sperm sample to the M well results in live sperm with sufficient motility to swim vertically down through the liquid buffer and through the porous membrane to the colorimetric agent. Evaluating the intensities of the color change of the colorimetric agents before and after contact with the sample gives a measure of total concentration of live sperm and motile sperm from which sperm motility is calculated.

31 Claims, 8 Drawing Sheets

(51) Int. Cl.
*G01N 33/52* (2006.01)
*G01N 21/78* (2006.01)
*G01N 15/06* (2006.01)
*C12N 5/076* (2010.01)
*G01N 30/00* (2006.01)
*C12N 5/071* (2010.01)
*G01N 15/00* (2006.01)
*G01N 33/487* (2006.01)
*G01N 21/77* (2006.01)

(52) U.S. Cl.
CPC ........... *C12N 5/0612* (2013.01); *G01N 15/06* (2013.01); *G01N 15/0606* (2013.01); *G01N 21/78* (2013.01); *G01N 30/00* (2013.01); *G01N 33/525* (2013.01); *B01L 2200/16* (2013.01); *B01L 2300/025* (2013.01); *B01L 2300/0627* (2013.01); *B01L 2300/161* (2013.01); *G01N 33/48707* (2013.01); *G01N 2015/0065* (2013.01); *G01N 2015/0681* (2013.01); *G01N 2015/0693* (2013.01); *G01N 2021/7793* (2013.01); *G01N 2800/367* (2013.01)

(58) Field of Classification Search
CPC ......... G01N 15/0606; G01N 33/48707; G01N 2015/0681; G01N 2800/367; G01N 2021/7793; G01N 2015/0693; G01N 2015/0065; C12N 5/0612; C12N 5/061; B01L 3/5023; B01L 2300/161; B01L 2300/0627; B01L 2300/025; B01L 2200/16
See application file for complete search history.

(56) References Cited

U.S. PATENT DOCUMENTS 5,935,800 A * 8/1999 Alvarez ................. A61D 19/00
422/422
2014/0212959 A1 7/2014 Matsuura et al.

FOREIGN PATENT DOCUMENTS

WO 2012126478 9/2012
WO 2014177157 11/2014

OTHER PUBLICATIONS

Asghr W, Velasco V, Kingsley JL, Shoukat MS, Shafiee H, Anchan RM, et al. Selection of Functional Human Sperm with Higher DNA Integrity and Fewer Reactive Oxygen Species. Adv Healthc Mater. 2014;3:1-9.
Coppola MA, Klotz KL, Kim K-AA, Cho HY, Kang J, Shetty J, et al. SpermCheck Fertility, an Immunodiagnostic home test that detects normozoospermia and severe oligozoospermia. Hum Reprod. 2010;25:853-61.
Björndahl L, Kirkman-Brown J, Hart G, Rattle S, Barratt CLR. Development of a novel home sperm test. Hum Reprod. 2006;21:145-9.
Nasr-Esfahani MH, Aboutorabi R, Esfandiari E, Mardani M. Sperm MTT viability assay: A new method for evaluation of human sperm viability. J Assist Reprod Genet. 2002;19:477-82.
Berridge M V., Herst PM, Tan AS. Tetrazolium dyes as tools in cell biology: New insights into their cellular reduction. Biotechnol Annu Rev. 2005;11:127-52.
Matsuura K, Chen K-HH, Tsai C-HH, Li W, Asano Y, Naruse K, et al. Paper-based diagnostic devices for evaluating the quality of human sperm. Microfluid Nanofluidics. 2014;16:857-67.
Nosrati et al.."Paper-based quantification of male fertility potential", Clinical chemistry 62 (3), pp. 458-465.
International Search Report for PCT/CA2016/051352 dated Mar. 6, 2017.
Written Opinion for PCT/CA2016/051352 dated Mar. 6, 2017.

* cited by examiner

DEVICES AND METHODS FOR QUANTIFICATION OF MALE FERTILITY

FIELD

The present disclosure relates to devices and methods for quantification of male fertility, and more particularly the present disclosure provides devices and methods for quantifying sperm motility.

BACKGROUND

The global burden of infertility is high, affecting more than 70 million couples (1,2). Male infertility accounts for 40-50% of infertility cases worldwide (3). Main causes of male infertility include low sperm count (azoospermia and oligozoospermia), poor vitality (necrozoospermia), low motility (asthenozoospermia), low DNA integrity, and abnormal sperm morphology (teratospermia) (4,5). Semen analysis to quantify these factors is the cornerstone of male infertility diagnosis (6), and also plays a critical role in monitoring male contraception after vasectomy to ensure permanent sterility (7).

Conventional techniques for semen analysis include counting chambers, computer assisted sperm analysis (CASA) (8), and vitality assays such as dye exclusion or hypotonic swelling (4,9). Cell counting chambers, namely hemocytometers and Makler chambers, are the traditional tools for quantification of sperm concentration and motility, working via manual visual inspection under a microscope. CASA systems use advanced optical microscopy to assess sperm concentration and motility via automatic online tracking of sperm in a digital image sequence (8,10). Dye exclusion methods use membrane-impermeable stains to selectively label dead cells (11). In hypotonic swelling, live sperm cells swell due to an influx of water to their cytoplasm from an induced osmotic pressure gradient (12). Both dye exclusion and hypotonic swelling vitality assays require manual microscopy inspection or flow cytometry to count the number of live and dead cells. All of these current semen analysis techniques suffer from several limitations, which prevent their widespread application: testing procedures are long and complex, testing requires expensive equipment, and the results are subjective, varying from clinician to clinician (13,14). Compliance of male patients to provide clinical samples is also low due to associated embarrassment and anxiety (7). A low cost and rapid test for semen analysis, suitable for both clinical and self-diagnosis, would have significant implications for patient care.

Microfluidic technologies have rapidly advanced diagnostic testing (15-17). In the context of fertility, traditional channel-based devices have been developed for sperm selection (18-22), embryo development (23-25), and semen analysis (14,26-28). Recently, paper has emerged as a scalable diagnostic platform (29-32). The home pregnancy test is the most widely used fertility-based diagnostic, enabling women to perform self-testing at their own discretion. Lateral flow assays have also been developed for home semen analysis; for example, SpermCheck and FertilMARQ use colorimetric signals to semi-quantitatively determine total sperm concentration within a sample (i.e. whether or not sperm concentration is higher than 20 million/mL) (33,34). Additionally, the Fertell assay measures motile sperm count by allowing sperm to swim up a fluid-filled reservoir towards a nitrocellulose-based immobilization region (35). Although effective, these technologies only inform on one semen parameter, while relying on user interpretation and costing up to 100 USD per test (13). There remains a need to provide a low cost, efficient means for assessing male fertility.

WO 2014/177157 discloses a device for analysis of cellular motility which involves a sample application compartment, a cell permeable filter, a conditioning medium, and analyzing chambers. The device test for motile cell concentration by allowing the motile population to swim from an initial sample through a cell permeable filter into a conditioning medium. The liquid in the conditioning medium will then be moved to an analyzing chamber where the cells will be separated from the liquid using a retaining filter. This concentration effect (retaining the cells on the upstream side of the filter) allows to visually observe the motile cells. The inventors suggest that a detection agent (such as a fluorescence dye or MTT) may be included in the conditioning medium or an optical detection may be integrated with the cell retaining filter for quantification of motile sperm concentration. While this device can be used to quantify motile sperm concentration, by separating motile from non-motile cells, the device only provides information related to one of the three critical indicators of male infertility, if used with human sperm.

WO 2012/126478 discloses a device for analysis of cellular motility which involves an inlet chamber which is in fluid communication with further analyzing chambers using a passage way. After applying the sample in the inlet chamber, a conditioning medium containing MTT is applied into the communication chambers. The device allows motile cells to swim through the passage way from the inlet chamber to the communication chambers which, after one hour, will produce a colorimetric signal correlated with motile sperm concentration in each of the analyzing chambers. The sample from each chamber will then pass through a vacuum filter. The color of the dried membrane filter can be used to quantify motile sperm concentration. The device disclosed in WO 2012/126478: (1) only quantified the motile sperm concentrations in analyzing chambers, (2) relies on an additional vacuuming step to concentrate the sperm on the filter for quantification, and (3) uses the MTT assay in bulk liquid which requires a long reaction time.

United States Patent Publication No. US 2014/0212959 to Matsuura discloses a device that measures sperm concentration using a thiazine dye (like Methylene Blue), and uses MTT to quantify sperm motility. The device tests for sperm motility by applying a sample of sperm at the center of the paper-based device and then allows the cells to swim through the paper. The paper is dry prior to applying the sample. As the sperm diffuse through the paper, there will be a change of color from yellow to purple. Motile sperm will be able to swim through the paper, away from the central part of the device where the sample is applied. Therefore, a sample with high number of motile sperm results in a flat gray-scale intensity profile, while a sample with low number of or no motile sperm results in a sharp intensity profile. Their technique relies on the ability of sperm to swim through the paper.

It would be very advantageous to provide a method and test device that simultaneously provides quantitative information related to live sperm concentration, motile sperm concentration, and sperm motility.

SUMMARY

This disclosure describes a low cost and rapid microfluidic based method and test device for quantifying male fertility potential. The test device is capable of simultaneously measuring three critical semen parameters rapidly, within only 10 minutes (min) namely live sperm concentration, motile sperm concentration, and sperm motility. The device can be paper-based making it very economical to make. The device may be purchased in retail outlets and used by the user without the need for a clinical setting.

In an embodiment there is provided a device for quantifying male fertility potential from a semen sample, comprising a transparent or semitransparent substrate layer and a first layer comprised of a hydrophilic porous material secured on top of the substrate layer, the first layer having first and second reaction spots spaced from each other and each reaction spot containing a colorimetric agent selected to undergo reaction with sperm such that upon reaction with sperm a color change occurs. The device includes a porous membrane covering the second reaction spot, with the membrane having pores in a size range from about 5 µm to about 14 µm. A second layer comprised of a hydrophilic porous material is secured on top of the first layer, with the second layer including first and second holes being located with respect to each other such that when the second layer is affixed to a top surface of the first layer the first and second holes are aligned with the first and second reaction spots. Upon application of a first portion of a semen sample directly to the first reaction spot through the hole in the second layer a color change occurs when live sperm is present, and upon application of a second portion of the semen sample through the second hole onto the membrane any change in color indicates motile sperm is present in the second portion that traversed through the porous membrane to contact the second reaction spot.

There is provided a method for quantifying fertility potential from a semen sample, comprising:

a) applying a first portion of a semen sample onto a colorimetric agent localized on a first reaction area on a support structure;

b) applying a second portion of the semen sample onto a second reaction area on the support structure, the second reaction area including a colorimetric agent localized on a second reaction area on the support structure and a porous membrane located on top of the colorimetric agent and a liquid buffer having sufficient viscosity to simulate in vivo fluid in the female tract located on top of the porous membrane such that motile sperm in the second portion of the semen sample must pass first through the liquid buffer and then the porous membrane to reach the colorimetric agent located on the second reaction area of the support structure, the porous membrane having pores in a size range from about 5 µm to about 14 µm; and c) observing any color change in the colorimetric agents localized on the first and second reaction areas, and when color changes are present, determining a concentration of live sperm on the first reaction area and determining a concentration of motile sperm on the second reaction area.

The present device may be sold in kit form which includes the device itself, the liquid buffer formulation in those embodiments where the membrane requires wetting prior to sample contact.

A further understanding of the functional and advantageous aspects of the present disclosure can be realized by reference to the following detailed description and drawings.

BRIEF DESCRIPTION OF THE DRAWINGS

Embodiments disclosed herein will be more fully understood from the following detailed description thereof taken in connection with the accompanying drawings, which form a part of this application, and in which.

DETAILED DESCRIPTION

Figure 1:
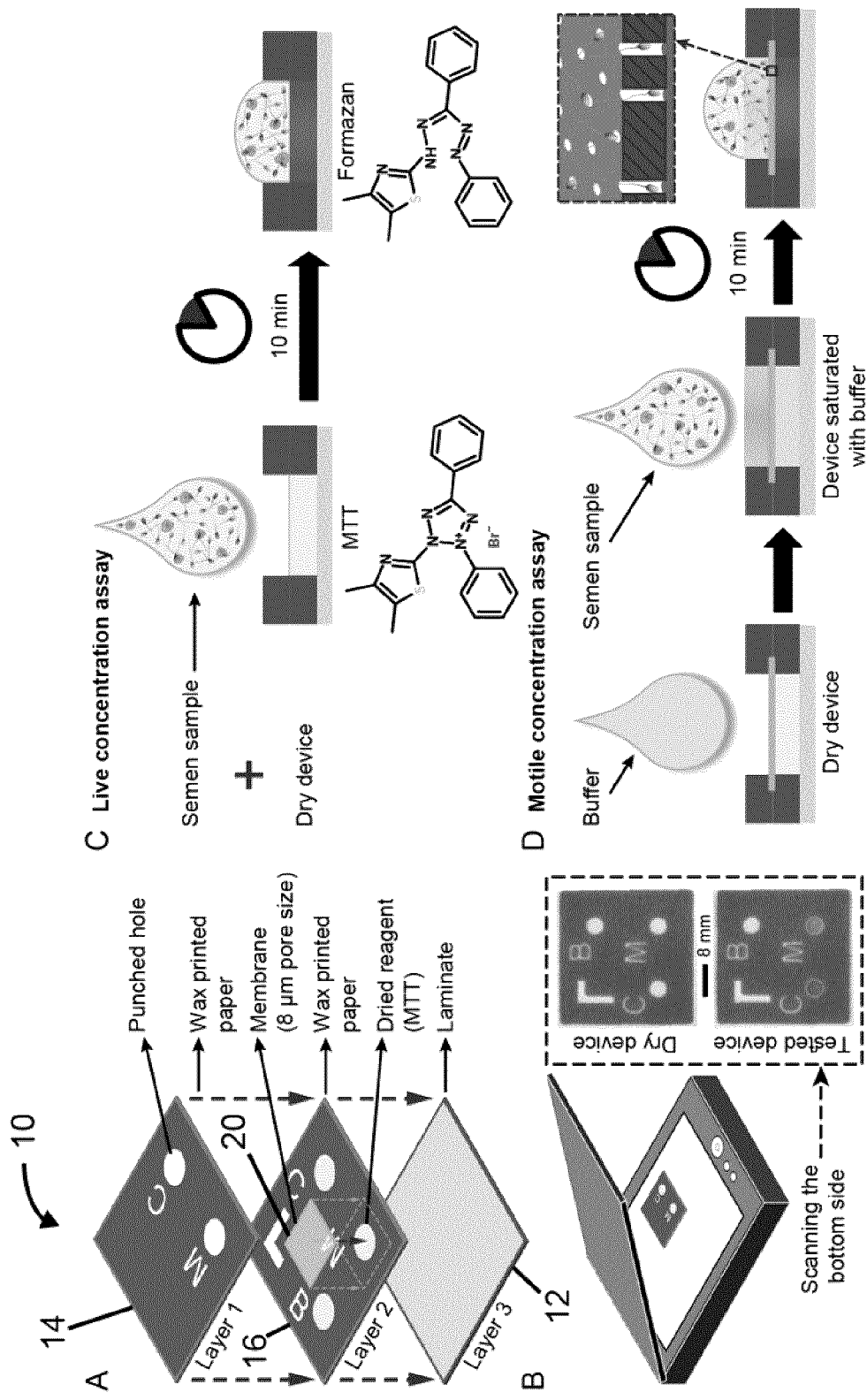
FIG. 1 shows a schematic of the paper-based semen analysis device and protocol. A) shows an exploded view of the 3D device. B) Shows a schematic view of the assembled device and images of devices before and 10 min after applying a semen sample. C) In the concentration spot, the semen sample is pipetted directly on the dried MTT in paper to generate a colorimetric signal. D) In the motility spot, sperm must swim through the high viscous buffer and relatively narrow (8-µm) pores within the membrane filter (shown inset) to reach the reaction spot and generate a colorimetric signal.

Various embodiments and aspects of the disclosure will be described with reference to details discussed below. The following description and drawings are illustrative of the disclosure and are not to be construed as limiting the disclosure. The drawings are not to scale. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions.

As used herein, the phrase "high viscosity buffer" refers to liquid buffer having sufficient viscosity to simulate in vivo fluid in the female tract and minimizes mixing and flow in the motility spot. Thus "high viscosity" means a buffer solution having a viscosity in a range from about 10 mPa s to about 250 mPa s. Non-limiting examples of "high viscosity" buffers that may be used include HEPES-buffered saline (HBS) solution, Human Tubal Fluid (HTF), Phosphate-buffered saline (PBS) solution, Bovine Serum Albumin (BSA), Dulbecco's Phosphate-Buffered Saline (DPBS) solution, Roswell Park Memorial Institute (RPMI) medium, and Beltsville Thawning Solution (BTS) supplemented with methyl cellulose (MC), hyaluronic acid (HA), dextran, ficoll, polyvinylpyrrolidone, and Carboxymethylcellulose to increase the viscosity.

As used herein, the phrases "motile cells" and "motility" refers to cells which are capable of moving through a liquid independent of any flow of the liquid itself. Thus "motile cells" are able to move in non-flowing liquids.

As used herein, the phrase "sperm motility" means the ratio of motile cell concentration to total cell concentration. The "sperm motility" reflects the fact that while there can be a large concentration of live cells, it is not necessarily the case that all these cells are able to propel.

The disclosure provides a low cost and rapid paper-based microfluidic approach for quantifying male fertility potential. In one embodiment, the invention provides microfluidic devices capable of simultaneously measuring three critical semen parameters rapidly, within only 10 minutes (min). These are live sperm concentration, motile sperm concentration, and sperm motility.

The device is robust and can tolerate a range of temperature and humidity conditions up to 16 weeks without losing functionality. Detection limits of 8.46 million/mL and 15.18 million/mL have been achieved for live sperm concentration and motile sperm concentration, respectively. The device provides clinical outcomes comparable to those of the conventional CASA and dye exclusion vitality assay. The invention provides paper-based technology that is a scalable alternative to conventional testing, suitable for self-screening of male fertility potential.

Device Fabrication

Referring to FIG. 1, a device for measuring sperm presence and mobility is shown generally at 10. Device 10 includes three layers including a transparent or partially transparent laminate layer 12 on the bottom, a first top layer 14 and and a second layer 16 sandwhiched between layers 12 and 14. patterned with wax on top. Second layer 16 includes three (3) reagent spots, a concentration reagent spot C, and motility spot M, and a background spot B, each of these spots having a layer of a colorimetric agent, discussed in more detail below. The background spot B, is to facilitate the process of quantification by providing information related to the color intensity of the dried colorimetric agent and without applying any sample. In an embodiment of the device, the background spot B can be avoided by the user acquiring two images of the device, one prior to, and one after applying the sample, and in this embodiment the image of each spot C and M after the test is compared to the image of each spot C and M prior to the test and the calculations are based on comparing these intensities.

For layers 14 and 16 device patterns were designed in AutoCAD and printed on paper (No. 1 Chromatography Paper, Sigma-Aldrich, Mo.) using a solid wax printer (ColorQube 8570N, Xerox Canada, Canada). Printed sheets of paper were then heated in an oven at 125° C. for 5 minutes to allow the wax to penetrate through the thickness of the paper sheets 14 and 16. A hole-puncher was used to punch two holes with 4 mm diameter in sheet 14, as access ports to spots in sheet 16 onto which the colorimetric agent is deposited. The adhesive laminate layer 12 was attached to the backside of layer 16. A 3 µL aliquot of 5 mg/mL solution of 3-(4,5-Dimethyl-2-thiazolyl)-2,5-diphenyl-tetrazolium bromide (MTT; Sigma-Aldrich, Mo., USA), prepared in distilled water, was dried on each of the 4 mm diameter background B, concentration C, and motility spots M in layer 16. Double sided tape was used to bond sheets 14 and 16 together. Prior to bonding, a 5 mm×5 mm membrane filter 20 with 8 µm pore size (Nuclepore track-etched polycarbonate membrane filter, Whatman—GE Healthcare Life Science, N.J., USA) was aligned on top of the motility spot and sandwiched between layers 14 and 16. Unlike the concentration and motility spots C and M respectively to which the semen samples are applied and contact in the case of live moving sperm, background spot B is not exposed as it serves as calibration, its intensity in the unreacted state is used to help calculate the concentration of sperm at C and M by comparison of the intensities of spots C and M compared to the unreacted colorimetric agents at B.

Device 10 may include a reservoir, activated by the user to release buffer onto the top of membrane 20. The reservoir may be a user-activated integrated reservoir mountedon the top of layer 14 that is connected via a channel to the to surface of membrane 20. It is noted that in embodiments of the test device a liquid buffer may not be required. For example, if the device includes a means of separately sealing the membrane to maintain its moisture while maintaining the rest of sensor system dry, for example by a removeable sheet seal that keeps moisture in the membrane, the liquid reagent may not be required to wet the membrane. Further, liquid reagent may not be required if membranes are used that can be sufficiently wetted by the original sample. Similarly, using membranes that do not require hydration may avoid the need for liquid reagents.

The substrate need not be paper, however the substrate needs to be a hydrophilic porous material since the device relies on the capillary action to wick the reagent solution, buffer and semen sample. Thus it will be appreciated that while layers 14 and 16 have been described as chromatographic paper, it will be appreciated that other types of papers, porous hydrophilic, and polymeric based materials may be used. The sheet material of sheets 14 and 16 may be any material that satisfy the functional requirements of power-free fluid transport (capillary action), light background color, and the ability to store reagents including but not limited to chromatography paper, filter paper, nitrocellulose and cellulose pads, printing papers, porous hydrophilic membranes, cloth, and other pulp-based materials from fiber crops, wood, or waste papers such as paper towels and tissue.

Further, it will be appreciated that the pore size of membrane filter 20 may vary between about 6 μm to about 12 μm for application of the device with human sperm. The pore size of the membrane is large enough to allow human sperm to swim through the membrane 20 and small enough to prevent the sperm in the semen sample to simply flow through the membrane into the layer 16. Therefore, the sperm needs to work to swim through membrane 20 to reach layer 16 and to generate a colorimetric signal in the motility spot, thereby showing its motility. The membrane filter 20 may be made of materials including but not limited to cyclopore polycarbonate, nuclepore polycarbonate, polycarbonate, cellulose acetate, regenerated cellulose, nylon, cellulose nitrate, polyamide, aluminum oxide, polytetrafluoroethylene (PTFE), nitrocellulose, mixed cellulose ester, glass, and cloth.

While the colorimetric agent above is 3-(4,5-Dimethyl-2-thiazolyl)-2,5-diphenyl-tetrazolium bromide (MTT), it will be understood that this is only exemplary. Other colorimetric agents include, but are not restricted to, salts of MTT. Non-limiting examples of other colorimetric agents include XTT or 2,3-Bis-(2-Methoxy-4-Nitro-5-Sulfophenyl)-2H-Tetrazolium-5-Carboxanilide; INT or 2-(4-iodophenyl)-3-(4-nitrophenyl)-5-phenyl-2H-tetrazolium chloride; MTS or 3-(4,5-dimethylthiazol-2-yl)-5-(3-carboxymethoxyphenyl)-2-(4-sulfophenyl)-2H-tetrazolium; TTC or 2,3,5-triphenyl-2H-tetrazolium chloride; NBT or Nitro blue tetrazolium; Methylene blue or methylthioninium chloride; and alamarBlue.

In the case of the application of the device with fluorescence readout methods, fluorescence viability dyes including but not limited to SYBR14, SYTO 9, Calcein AM, and Propidium iodide can be used.

Device 10 may be read using any smart phone having a camera incorporated therein, such as an Apple iPhone, Samsung Galaxy (all series), Sony Xperia, HTC smartphones, LG smartphones, Motorola smartphones, Microsoft Lumia, Huawei smartphones, BlackBerry Smartphones.

Figure 7:
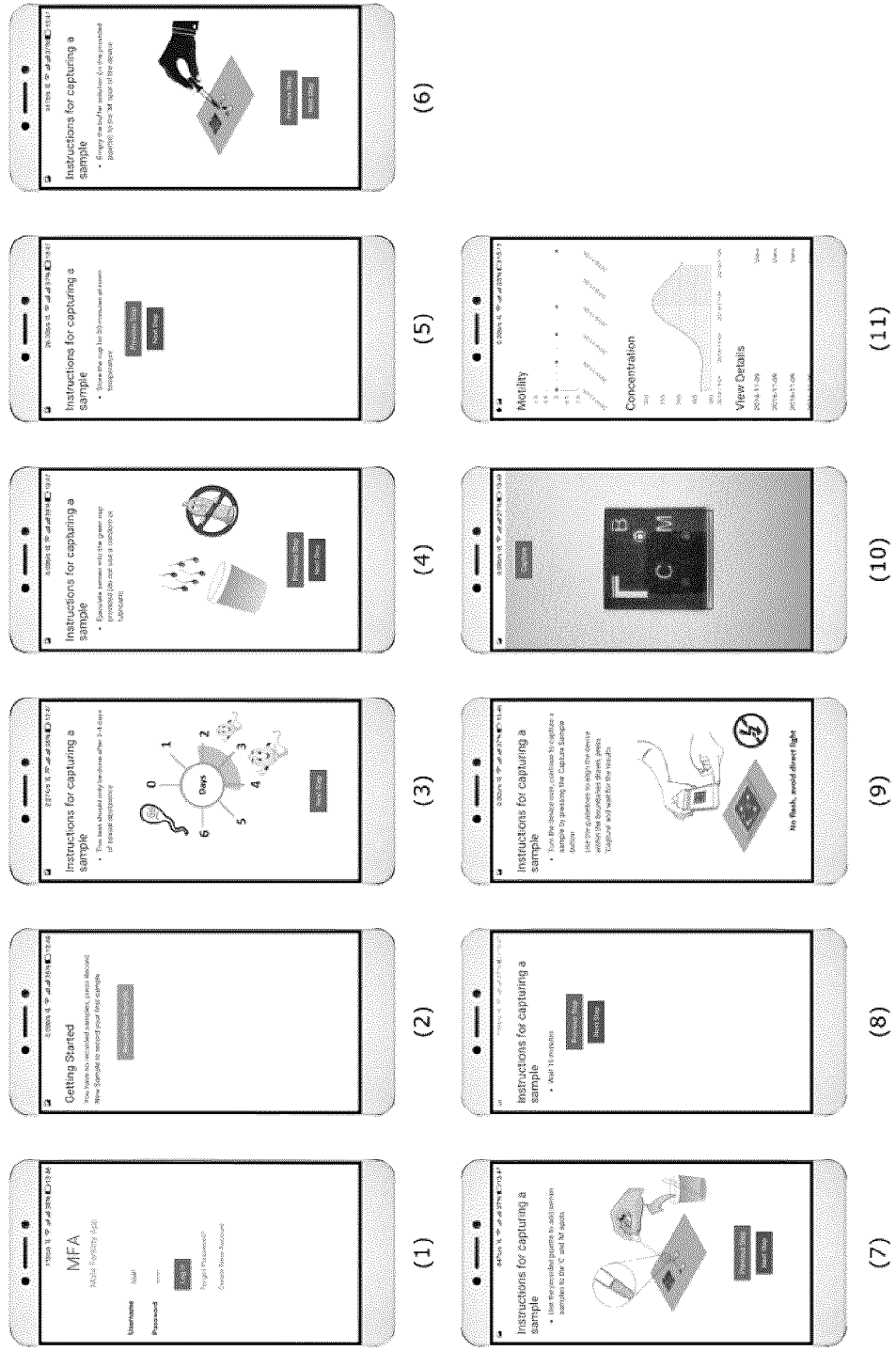
FIG. 7 shows a series of screen shots of a smart phone illustrating a smart phone having an application downloaded thereto for providing instructions to a user to carry the semen test.

FIG. 7 shows a series of screen shots of a smart phone illustrating a smart phone having an application downloaded thereto for providing instructions to a user to carry the semen test when the smartphone based camera is used to take visual images of the spots B, C and M to determine sperm motility. This application allows the user to create a user account, protected with a password, to serve as a link between the application and his personal data. The application asks the user to test the device after 2-4 days of sexual abstinence to provide him with reliable data related to his fertility potential. The application provides the user with instructions for collecting the sample to ensure that the user does not use a condom or lubricant and allows 30 minutes for liquefaction. Following this step, the application will provide a step-by-step instruction for applying the buffer on the motility spot, applying the semen sample on the concentration and motility spot, and capturing a proper image using predefined guidelines. The application will analyze the image by measuring the gray scale intensity of background, concentration, and motility spots, and provide the user with quantitative values of live sperm concentration, motile sperm concentration, and sperm motility.

Figure 3:
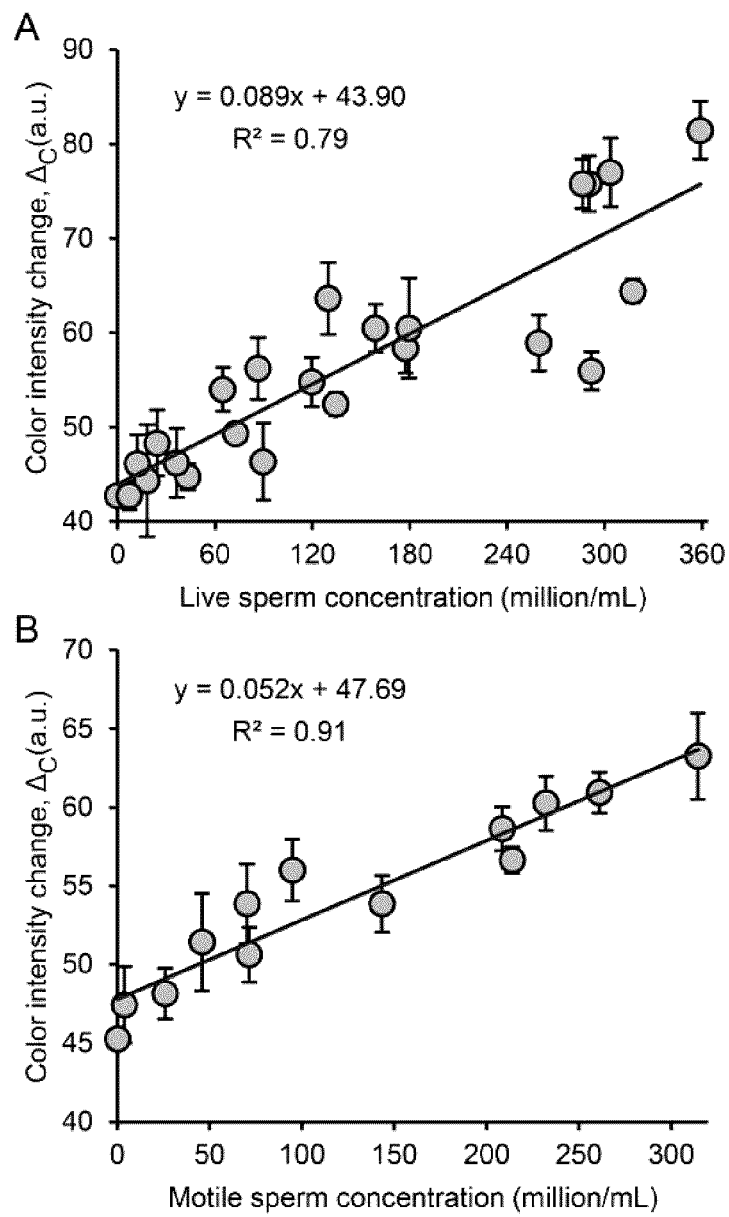
FIG. 3 shows calibration curves. A) Calibration curve for live sperm concentration using $\Delta_C$ between concentration (C) and background (B) spots. The limit of detection (LOD) for live sperm concentration is 8.46 million/mL. B) Calibration curve for motile sperm concentration using $\Delta_C$ between motility (M) and background (B) spots. The LOD for motile sperm concentration is 15.18 million/mL. Each data point is an average of four independent measurements with error bars as one standard deviation.
Figure 8:
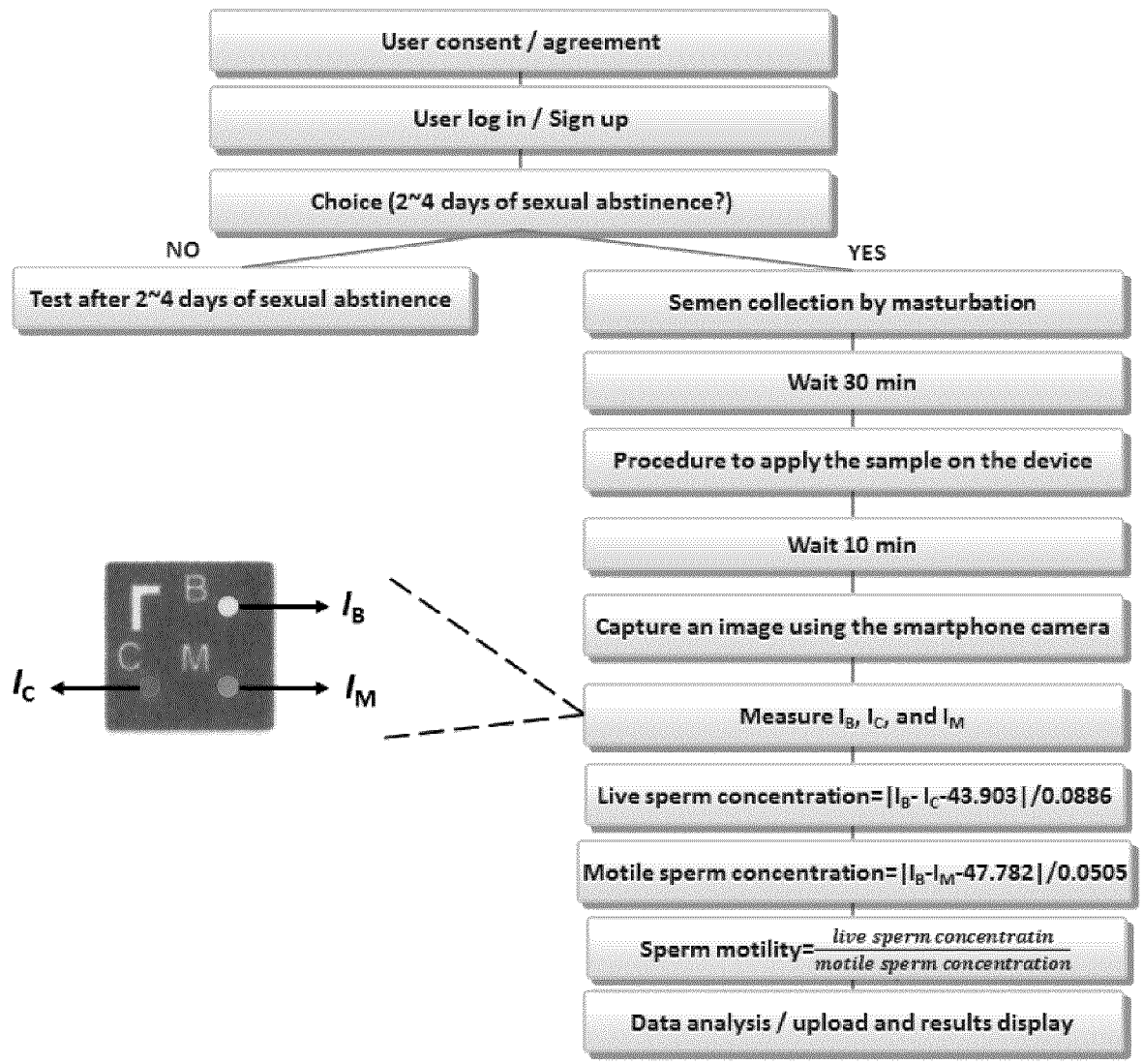
FIG. 8 is a flowchart showing the steps of the method used to quantify semen parameters by processing the images of the test device using the smart phone camera.

The flowchart of FIG. 8 shows the steps that the smartphone is programmed with to quantify live sperm concentration, motile sperm concentration, and sperm motility. By capturing a proper image using predefined guidelines, the application can locate Background B, Concentration C, and Motility M spots. The average intensity of the image over the area of B, C, and M will be calculated, respectively represented by $I_B$, $I_C$, and $I_M$. The application will use the equation obtained from the calibration curve in FIG. 3A to calculate live sperm concentration as $(I_B-I_C-43.903)/0.0886$. The application will use the equation obtained from the calibration curve in FIG. 3B to calculate motile sperm concentration as $(I_B-I_M-47.782)/0.0505$. Sperm motility will be quantified as the ratio of motile sperm concentration to live sperm concentration. The calibration equations from FIG. 3 may change for application of the device with different colorimetric agents or buffers, and may improve as more data points are being included in the curve over time.

The application also enables the user to monitor the quality of his sample over the time. The application will potentially ask the user to optionally provide information related to his age, marital status, education, occupation, ethnicity, geographical location, medical history, and lifestyle habits such as smoking, drinking, and drug abuse.

The present method and device will now be illustrated with the following example studies on actual male subjects.

Materials and Methods

Human Semen Preparation

Frozen human semen was used to characterize the device performance. Cryogenically frozen human semen was purchased in 1 mL vials from ReproMed Ltd. (Toronto, Canada) and stored in liquid nitrogen. All donors provided consent for research participation in accordance with regulations of Assisted Human Reproduction Act. Human semen vials was thawed for 5 min in 37° C. water bath prior to experiments. Human semen with 50 million/mL concentration and 40% motility was used in the experiment. Fresh human semen samples from patients (n=5) and healthy donors (n=12) were obtained by masturbation after 2-4 days of sexual abstinence at the Urology Research Laboratory, Royal Victoria Hospital, Canada. All donors and patients signed and informed consent, and the information for this study remains confidential within the institution. Samples were incubated at 37° C. for 30 min to allow liquefaction. HEPES buffered salt (HBS) solution (135 mM NaCl, 5 mM KCl, 12 mM D-Glucose, 25 mM HEPES, 0.75 mM $Na_2HPO_4 \cdot 2H_2O$; Sigma-Aldrich, Mo.) supplemented with 1 mg/mL Poly(vinyl Alcohol) (Sigma-Aldrich, Mo.) and 0.5% methyl cellulose (M0512; Sigma-Aldrich, Mo.) was used to prepare different dilutions of semen and also used as the buffer in the motility assay. All the experiments were conducted at room temperature and within 10 min of liquefaction/thawing.

Alternatively, the buffer addition step above may be achieved or avoided through (a) release of buffer from an integrated reservoir, activated by the user; (b) a user-activated integrated reservoir that is connected via a channel to the membrane; (c) means of separately sealing the membrane to maintain its moisture while maintaining the rest of sensor system dry; (d) alternative means or membranes that can be sufficiently wet by the original sample; (e) alternative membranes that do not require hydration.

Human Semen Analysis

Semen samples were analyzed for concentration and motility using computer assisted sperm analysis (CASA). A CASA system (Penetrating Innovations, Ingersoll, Canada) equipped with an Olympus BH2 Microscope, Minitub Accupixel camera, and a Sperm Vision HR software (Version 1.0.5, 2008) was used to obtain standard semen parameters in accordance to WHO guidelines. Semen samples were analyzed for vitality using a dye exclusion assay. Briefly, 10 µL of the eosin-nigrosin stain (0.65% eosin Y and 10% nigrosin in distilled water) was mixed with 10 µL of semen sample and the suspension was smeared on glass slides and allowed to air-dry. Manual visual inspection under a microscope was used to count live and dead sperm. Sperm were scored as live if luminous or unstained and dead if stained pink or red. At least 200 cells were counted and percent vitality was calculated.

Data Analysis

The laminate side of tested devices were scanned with a letter sized scanner (CanoScan 9000F, Canon) for quantification through the transparent or semitransparent laminate 12. For characterization experiments, devices were scanned before and 10 min after applying the sample. Freely available image processing software ImageJ was used to obtain the color intensity of the background spot, $I_B$, concentration spot, $I_C$, and motility spot, $I_M$, for each device. The difference in color intensity between the background and concentration spots, $I_B$-$I_C$, was used for quantification of live sperm concentration. The difference in color intensity between background and motility spots, $I_B$-$I_M$, was used for quantification of motile sperm concentration. The ratio of motile sperm concentration to live sperm concentration was used to quantify motility. Data quantification was completed in Microsoft Excel.

Results and Discussion

Live and Motile Sperm Concentration Assays

The device is a multi-layer porous composite to simultaneously measure live and motile sperm concentration, and sperm motility. The exploded view of the device is shown in FIG. 1a. Two layers of wax printed paper were stacked using double-sided tape (layers 14 and 16 in FIG. 1a). Upper layer 14 includes two punched through-holes which provide access to distinct reaction spots for concentration (C) and motility (M) assays. Lower layer 16 contains the C and M spots embedded with 3 µL of 5 mg/mL 3-(4,5-Dimethyl-2-thiazolyl)-2,5-diphenyl-tetrazolium bromide (MTT). A background signal spot (B) was also embedded with the MTT solution as a reference color and for image analysis. Prior to bonding layers 14 and 16, the porous membrane filter 20 with 8 µm pore size was aligned on top of the motility spot (M). The transparent adhesive laminate layer 12 covers the bottom side of the layer 16 to limit evaporation and facilitate imaging (FIG. 1b). This simple design and fabrication process requires minimal reagents, expertise, and equipment, with a total material cost of ~0.05 USD per device.

Readout from the device is achieved using the enzymatic colorimetric MTT assay. Briefly, the yellow MTT tetrazolium converts to purple formazan upon removal of the bromide by diaphorase flavoprotein enzyme present in metabolically active human sperm (36-38). This colorimetric signal from the MTT assay is shown to be strongly correlated with the established sperm vitality assays such as eosin-nigrosin and hypo-osmotic swelling (36,39). The paper-based semen analysis device tests simultaneously for live sperm concentration and motile sperm concentration in two distinct spots in 10 min. In the concentration spot, the semen sample is pipetted directly on the dried MTT to generate a colorimetric signal (FIG. 1c).

In the motility spot, prior to applying the semen sample, a high viscosity buffer is pipetted to saturate the paper and the membrane filter below, forming a reservoir in layer 14 (FIG. 1d). Sperm must swim vertically through the viscous buffer in layer 14 and then through the narrow 8 µm pore sized membrane filter to generate a colorimetric signal. The high viscosity buffer simulates in vivo fluid in the female tract and minimizes mixing and flow in the motility spot. After 10 min, the back side of transparent or semitransparent layer 12 of the device 10 is scanned for quantification of colorimetric signals. The differences between color intensities of the concentration and motility spots C and M with respect to the color intensity of the background spot B quantify the live and motile sperm concentrations, respectively.

Figure 2:
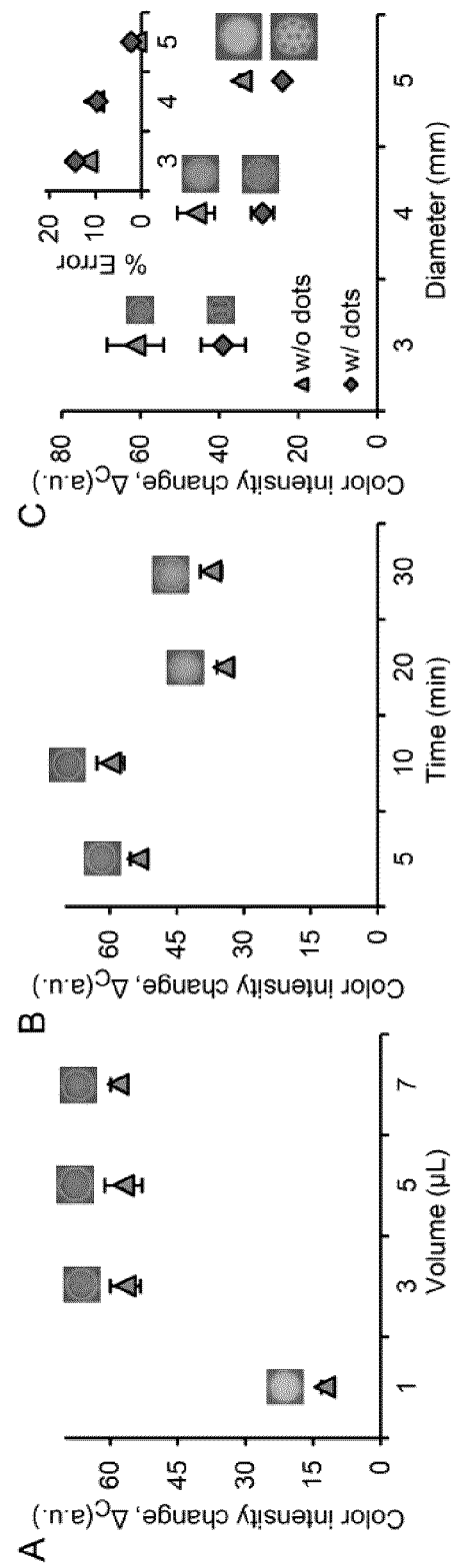
FIG. 2 shows graphical data which characterize the operating parameters of the paper-based semen analysis device. A) $\Delta_C$ as a function of sample volume. B) $\Delta_C$ as a function of reaction time. C) $\Delta_C$ color intensity as a function of reaction spot diameter and patterned dots. Each data point is an average of four independent measurements with error bars as one standard deviation. The values of $\Delta_C$ were calculated by taking the difference between the concentration and background spots.

FIG. 2 shows the characterization of the operating parameters for the paper-based semen analysis device using human semen samples. With respect to the sample volume, the difference in color intensity as compared to the background spot ($\Delta_C$) increased more than 350% from 12.2 for 1 µL sample volume to 56.6 for 3 µL sample volume and plateaued thereafter (FIG. 2a), using devices with 4 mm diameter reaction spots and a 10 min reaction time. With regard to reaction time, $\Delta_C$ increased about 11% by increasing the reaction time from 5 min to 10 min (FIG. 2b), using devices with 4 mm diameter reaction spots and by applying 3 µL sample volume. However, $\Delta_C$ decreased about 40% by further increasing the reaction time to 20-30 min. This drop in color intensity over long reaction times is attributed to evaporation of liquid which consistently caused discoloration in this manner. Devices were fabricated and tested with 3 mm, 4 mm, and 5 mm reaction spot diameters and for spots both with and without patterned dots, as shown in FIG. 2c. The results indicate that both $\Delta_C$ and associated error (as shown inset in FIG. 2c) decreased with increasing reaction spot diameter. Dots can improve readout by pinning the interface during evaporation (40). Here, however, devices without dots resulted in 43-56% higher $\Delta_C$ as compared with patterned dots. Based on this characterization, these operating parameters were selected for all subsequent experiments: devices with 4 mm diameter reaction spots without patterned dots, 3 µL sample volume, and 10 min reaction time.

Clinical Assessment with Human Semen Samples

The paper-based semen analysis device was tested with raw human semen samples at the Royal Victoria Hospital in Montreal, Canada. Current clinical practices (CASA and dye exclusion assay) were used to assess concentration, vitality, and motility of each sample in parallel with the device. FIG. 3a shows the calibration curve for live sperm concentration, ranging from 7.27 million/mL to 359 million/mL (with total concentrations and viabilities ranging from 8.56 million/mL to 381 million/mL and 52% to 94%, respectively). FIG. 3b shows the calibration curve for motile sperm concentration, ranging from 3.73 million/mL to 315 million/mL (with motility ranging from 9% to 87%).

The limits of detection (LOD) for the live and motile sperm concentration assays were calculated using three times the standard deviation of the signal from a blank device with zero sperm concentration (i.e. applying only buffer on the concentration and motility spots and scanning after 10 min). These values were 8.46 million/mL for live sperm concentration and 15.18 million/mL for motile sperm concentration. Based on reference values for human semen characteristics from the World Health Organization (WHO), the lower reference limits for live sperm concentration and motile sperm concentration are 8.7 million/mL and 6 million/mL, respectively (resulting from respective threshold values of 15 million/mL for total concentration, 58% for vitality, and 40% for motility) (4). Considering these limits and the LOD of our device, a detectable color change in the concentration and motility spots indicates that the patient has sufficient fertility potential. In contrast, if no detectable color change is observed, then that patient may be at high risk for azoospermia, oligozoospermia, necrozoospermia, or asthenozoospermia.

Figure 4:
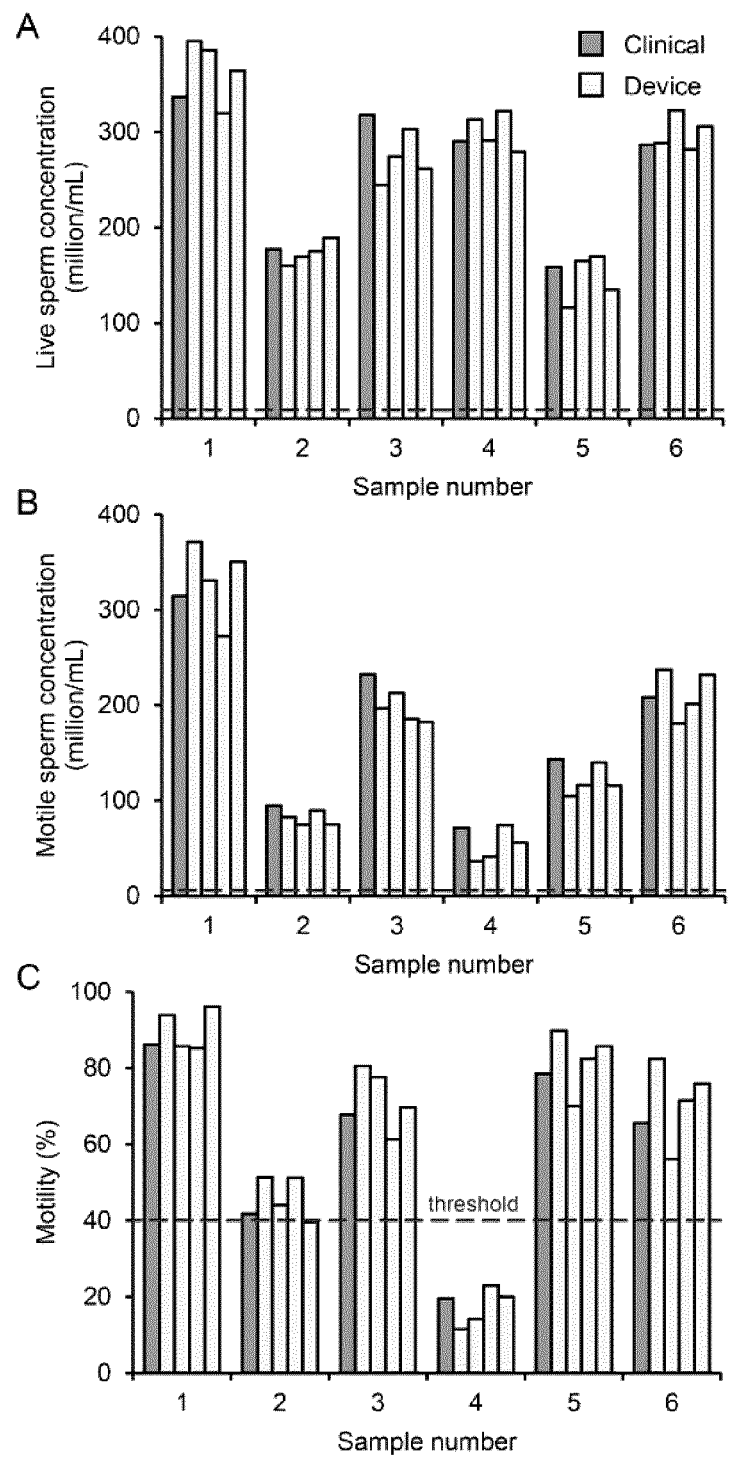
FIG. 4 shows clinical assessment of the paper-based semen analysis device. Direct comparison of A) live sperm concentration, B) motile sperm concentration, and C) motility values measured with the device to those measured with standard clinical approaches. For each sample, four devices (white bars) were tested in parallel with the clinical testing (blue bars). Live and motile sperm concentration values for tested devices were calculated using the linear calibration equations in FIG. 3. Motility values for tested devices were calculated by dividing live sperm concentration with motile sperm concentration. Dashed lines indicate the WHO lower reference limits for human semen parameters.
Figure 6:
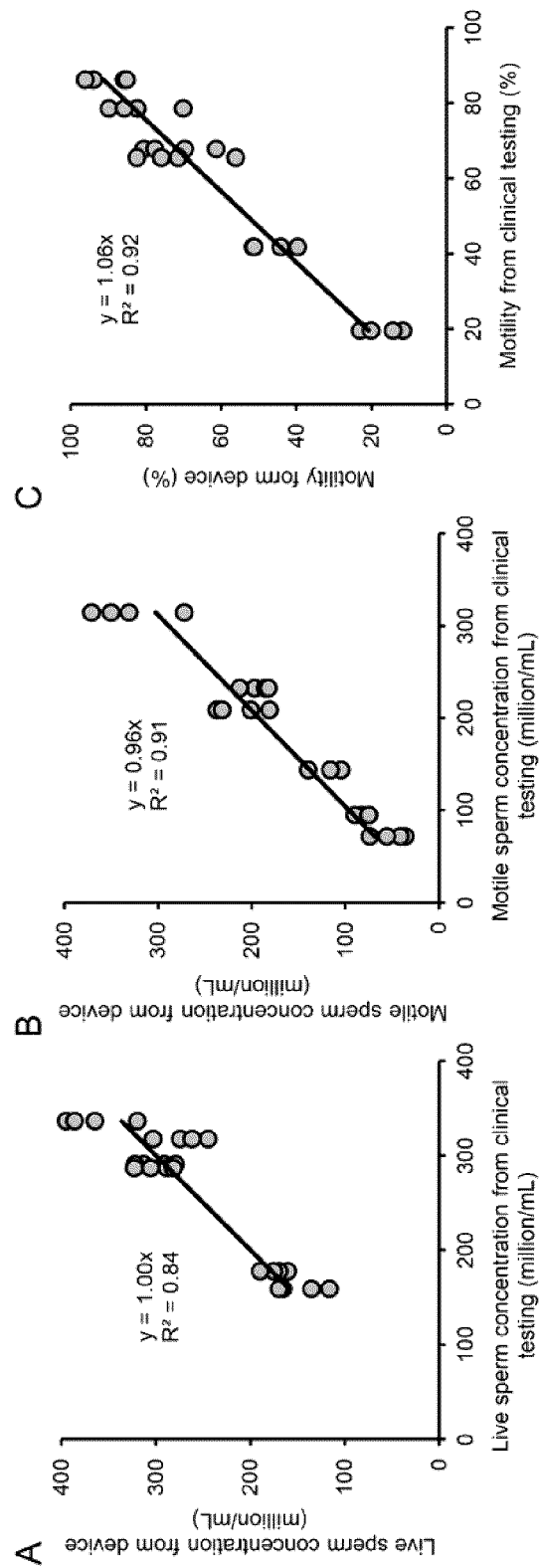
FIG. 6 shows clinical assessment of the paper-membrane composite semen analysis device. A) Live sperm concentration, B) motile sperm concentration, and C) motility values measured with the device as compared with those measured with standard clinical approaches.

FIG. 4 compares live sperm concentration, motile sperm concentration, and motility measured by both the device and standard clinical approaches. For each clinical sample, four devices were tested in parallel, and motility values from the device were calculated by dividing the motile sperm concentration with the live sperm concentration. Results from our paper-based semen analysis device strongly correlate to clinical data from CASA and dye exclusion vitality assays run in parallel (with respective $R^2$ values of 0.84, 0.91, and 0.92 for live sperm concentration, motile sperm concentration, and motility as shown in FIG. 6). Our device provides 100% agreement in terms of clinical outcome for patients. In addition, the device provides quantitative information related to sperm motility, which is not possible with existing commercial paper-based devices. A lower reference limit of 40% is defined by WHO for motility (4), which is used in clinics as a threshold value for poor motility and a diagnostic threshold for male-factor infertility. As shown in FIG. 4c, sample number 4, while indicating appropriate live and motile sperm concentration, would be recommended for assisted reproduction based on both device and clinical motility results. Collectively, our paper-based semen analysis device reliably informs on three critical male fertility parameters, and can be used for rapid clinical testing with additional potential in self-screening.

Robustness in Demanding Conditions

Figure 5:
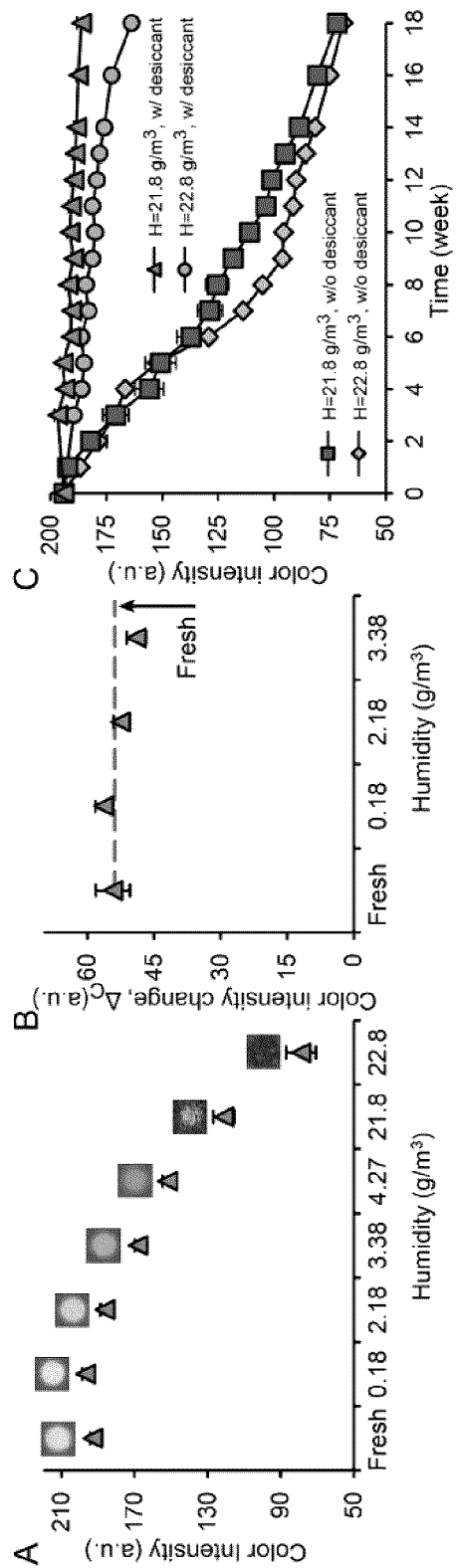
FIG. 5 shows robustness of the paper-based semen analysis device. A) Color intensity of the reaction spots as a function of humidity of the storage environments after 8 weeks of storage. B) $\Delta_C$ of the devices that passed the storage test in comparison with the signals from fresh devices fabricated same day (dashed line). C) Color intensity of the reaction spots over time for devices stored with and without desiccant in environments with 21.8 g/m$^3$ and 22.8 g/m$^3$ humidity. Each data point is an average of four independent measurements with error bars as one standard deviation. The values of $\Delta_C$ were calculated by taking the difference between the concentration and background spots.

The robustness of the paper-based semen analysis device was tested in challenging conditions. Specifically, high humidity and air temperature can both discolour paper and degrade dried reagents in paper-based devices (29). Table 1 summarizes the results over 8 weeks of storage as a function of temperature and humidity conditions. The color intensity of each stored device was compared to devices fabricated the same day ('fresh'). FIG. 5a shows the colour intensity as a function of humidity. Devices stored in an absolute humidity of lower than 3.38 g/m$^3$, regardless of the storage temperature, showed less than 10% change in the color intensity of the reaction spots—deemed a 'pass' in Table 1. The resulting signal from testing the 'passed' devices with human semen is shown in FIG. 5b, with output comparable to otherwise identical test with newly fabricated devices.

TABLE 1

Robustness of the paper-based semen analysis device after 8 weeks of storage in different humidity and temperature conditions.

| Storage condition | Temperature (° C.) | Absolute Humidity (g/m$^3$) | Condition |
|---|---|---|---|
| Freezer | −20 | 0.18 | Pass |
| Room - Normal | 24 | 2.18 | Pass |

TABLE 1-continued

Robustness of the paper-based semen analysis device after 8 weeks of storage in different humidity and temperature conditions.

| Storage condition | Temperature (° C.) | Absolute Humidity (g/m$^3$) | Condition |
|---|---|---|---|
| Incubator 1 | 32 | 3.38 | Pass |
| Fridge | 12 | 4.27 | Fail |
| Room - Saturated | 24 | 21.80 | Fail |
| Incubator 2 | 30 | 22.80 | Fail |

At absolute humidities above 3.38 g/m$^3$, the color intensity of the reaction spots decreased with increasing humidity. For these devices, the change of color in the reaction spots from yellow to purple suggests that in such highly humid environments MTT is converted to insoluble formazan over time. This humidity-dependent instability of the device, when stored in humid conditions, can be resolved by packaging the device with desiccant in a sealed plastic bag. FIG. 5c shows color intensity of the reaction spots over time for devices stored with and without desiccant in environments with 21.8 g/m$^3$ and 22.8 g/m$^3$ absolute humidities (highest humidities tested in our 8 week robustness test). Results indicate that devices stored with desiccant showed less than 10% decrease in the color intensity of the reaction spots after 16 weeks of storage. However, devices stored without desiccant showed more than 12% drop in the color intensity after only 2 weeks of storage and more than 60% drop after 18 weeks. The color intensity for devices stored at 22.8 g/m$^3$ absolute humidity started to decline after 16 weeks, the point at which the desiccant reached its moisture capacity. Altogether, these results indicate that packaging the device with desiccant maintains the functionality of the device up to four months in humid conditions.

While the device and method described above have been exemplified using human males as an example, it will be appreciated that the present device and method may have applications to veterinary medicine. Table 2 below shows a table of sperm sized of various animals, and these sizes would determine the range of pore sizes that can be used in the membrane. Thus, for the application of the device with semen sample from other species with smaller and larger sperm size than human, the pore size of the membrane filter 20 may vary between 5 µm and 14 µm.

TABLE 2

Table of sperm sizes, approximately, a related membrane pore size range to be used for the motility assay (in case of animal testing, different chemicals might be used than what is suggested for human): Data from *Journal of Reproduction & Fertility* (1985) 75, 153.

| Species | Sperm head size (µm) | | Pore size of the membrane in the device (µm) |
|---|---|---|---|
| | Major axis | Minor axis | |
| Human | 6.1 | 3.5 | 5-12 |
| Bovine | 8.5 | 4.3 | 7-13 |
| Buffalo | 9.4 | 5.0 | 8-14 |
| Pig | 8.5 | 4.2 | 7-13 |
| Horse | 7.0 | 3.9 | 6-12 |
| Mouse | 5.5 | 3.4 | 4-10 |

The present device may be sold in kit form which includes the device itself, the liquid buffer formulation in those embodiments where the membrane requires wetting prior to sample contact. The liquid formulation may be packaged in a separate container along with the device wherein the user opens the container and dispenses the liquid on the membrane prior to contacting the semen sample to the top of the liquid buffer solution. Alternatively the device may be produced with a sealed integrated buffer reservoir which is in flow communication with the top of the membrane when the membrane is exposed prior to use of the device. The packaging can include instructions to the user regarding how to download the software package to be loaded onto the user's computer or smart phone so that upon taking visual images of the three sites C, M and B, the intensities can be used to calculate concentration of live sperm, concentration of motile sperm and sperm motility.

The kit may include a collection cup for collecting the semen from the user and a pipette for dispensing the semen from the collection cup onto the first reaction area and onto a top of the porous membrane and optionally on top of the liquid buffer layer when the liquid buffer is used.

Summary

The inventors have demonstrated a low cost and rapid paper-based microfluidic approach for quantifying male fertility potential, simultaneously measuring three critical semen parameters in 10 min: live sperm concentration, motile sperm concentration, and sperm motility. Detection limits of 8.46 million/mL and 15.18 million/mL were achieved for live sperm concentration and motile sperm concentration, respectively. The present paper-based semen analysis device provided identical clinical outcomes as the conventional CASA and dye exclusion vitality assay ($R^2>0.84$). The device outperforms existing commercial paper-based devices by providing quantitative information related to sperm motility. The device is also robust and can tolerate a range of temperature conditions without losing functionality. It can withstand high absolute humidity conditions (22.8 $g/m^3$) for over 16 weeks when packaged with desiccant. The paper-based technology disclosed herein is an attractive alternative to much more expensive conventional laboratory testing, with additional potential for self-screening of male fertility potential.

The present device and method is advantageous compared to known methods. For example, the device disclosed in WO 2014/177157, is used to quantify motile sperm concentration, by separating motile from non-motile cells, the device only provides information related to one of the three critical indicators of male infertility, if used with human sperm. In contrast, the present device and method tests simultaneously for three critical semen parameters within 10 min and provides quantitative information related to live sperm concentration, motile sperm concentration, and sperm motility by integrating a colorimetric assay in a microfluidic platform.

With respect to WO 2012/126478 which only quantifies the motile sperm concentrations in analyzing chambers, relies on a vacuuming step to concentrate the sperm on the filter for quantification, and uses the MTT assay in bulk liquid which requires a long reaction time, the method and device disclosed herein provides information related to all three critical semen parameters by quantifying live sperm concentration and sperm motility, on top of measuring motile sperm concentration that can be quantified using the prior art disclosed in WO 2012/126478. This capability enables the present method and device to differentiate between patients with high concentrations and low motility.

A significant difference between the present method and device and the device of US 2014/0212959 in addition to the fact that, like the two above-mentioned references, it does not measure total sperm concentration, is that the present method and device tests for motility by having the sperm cells to swim vertically through a pool of buffer and then through the pores of the membrane to reach the top surface of the second layer of the paper, where the colorimetric reagent is located.

REFERENCES

1. Mascarenhas M N, Flaxman S R, Boerma T, Vanderpoel S, Stevens G a. National, Regional, and Global Trends in Infertility Prevalence Since 1990: A Systematic Analysis of 277 Health Surveys. Low N, editor. PLoS Med. 2012; 9:e1001356.
2. Ombelet W, Cooke I, Dyer S, Serour G, Devroey P. Infertility and the provision of infertility medical services in developing countries. Hum Reprod Update. 2008; 14:605-21.
3. Schultz R M. The Science of ART. Science (80-). 2002; 296:2188-90.
4. WHO laboratory manual for the Examination and processing of human semen. 5th ed. Geneva: WHO Press; 2010.
5. Agarwal A, Said T M. Role of sperm chromatin abnormalities and DNA damage in male infertility. Hum Reprod Update. 2003; 9:331-45.
6. De Jonge C. Semen analysis: looking for an upgrade in class. Fertil Steril. 2012; 97:260-6.
7. Maatman T J, Aldrin L, Carothers G G. Patient noncompliance after vasectomy. Fertil Steril. 1997; 68:552-5.
8. Kime D E, Van Look K J, McAllister B G, Huyskens G, Rurangwa E, Ollevier F. Computer-assisted sperm analysis (CASA) as a tool for monitoring sperm quality in fish. Comp Biochem Physiol C Toxicol Pharmacol. 2001; 130:425-33.
9. Vasan S S. Semen analysis and sperm function tests: How much to test? Indian J Urol. 2011; 27:41-8.
10. Amann R P, Katz D F. Andrology Lab Corner: Reflections on CASA What is CASA? J Androl. 2004; 25:317-25.
11. Bjorndahl L, Soderlund I, Kvist U. Evaluation of the one-step eosin-nigrosin staining technique for human sperm vitality assessment. Hum Reprod. 2003; 18:813-6.
12. Jeyendran R S, Van der Ven H H, Perez-Pelaez M, Crabo B G, Zaneveld L J. Development of an assay to assess the functional integrity of the human sperm membrane and its relationship to other semen characteristics. J Reprod Fertil. 1984; 70:219-28.
13. Brezina P R, Haberl E, Wallach E. At home testing: Optimizing management for the infertility physician. Fertil Steril. 2011; 95:1867-78.
14. Chen C-Y, Chiang T-C, Lin C-M, Lin S-S, Jong D-S, Tsai V F-S, et al. Sperm quality assessment via separation and sedimentation in a microfluidic device. Analyst. 2013; 138:4967-74.
15. Sackmann E K, Fulton A L, Beebe D J. The present and future role of microfluidics in biomedical research. Nature. Nature Publishing Group; 2014; 507:181-9.
16. Gong M M, MacDonald B D, Vu Nguyen T, Sinton D. Hand-powered microfluidics: A membrane pump with a patient-to-chip syringe interface. Biomicrofluidics. 2012; 6:044102.

17. Gong M M, MacDonald B D, Vu Nguyen T, Van Nguyen K, Sinton D. Field tested milliliter-scale blood filtration device for point-of-care applications. Biomicrofluidics. 2013; 7:1-11.
18. Nosrati R, Vollmer M, Eamer L, San Gabriel M C, Zeidan K, Zini A, et al. Rapid selection of sperm with high DNA integrity. Lab Chip. 2014; 14:1142-50.
19. Tasoglu S, Safaee H, Zhang X, Kingsley J L, Catalano P N, Gurkan U A, et al. Exhaustion of racing sperm in nature-mimicking microfluidic channels during sorting. Small. 2013; 9:3374-84.
20. Knowlton S M, Sadasivam M, Tasoglu S. Microfluidics for sperm research. Trends Biotechnol. Elsevier Ltd; 2015; 33:221-9.
21. Asghar W, Velasco V, Kingsley J L, Shoukat M S, Shafiee H, Anchan R M, et al. Selection of Functional Human Sperm with Higher DNA Integrity and Fewer Reactive Oxygen Species. Adv Healthc Mater. 2014; 3:1-9.
22. Eamer L, Nosrati R, Vollmer M, Zini A, Sinton D. Microfluidic assessment of swimming media for motility-based sperm selection. Biomicrofluidics. 2015; 9:044113.
23. Han C, Zhang Q, Ma R, Xie L, Qiu T, Wang L, et al. Integration of single oocyte trapping, in vitro fertilization and embryo culture in a microwell-structured microfluidic device. Lab Chip. 2010; 10:2848-54.
24. Ma R, Xie L, Han C, Su K, Qiu T, Wang L, et al. In vitro fertilization on a single-oocyte positioning system integrated with motile sperm selection and early embryo development. Anal Chem. 2011; 83:2964-70.
25. Lai D, Chiu J H-C, Smith G D, Takayama S. Microfluidics for Assisted Reproductive Technologies. In: van den Berg A, Segernik L, editors. Microfluid Med Appl. Cambridge, UK, UK: Royal Society of Chemistry; 2015. page 131-48.
26. Segerink L I, Sprenkels A J, ter Braak P M, Vermes I, van den Berg A. On-chip determination of spermatozoa concentration using electrical impedance measurements. Lab Chip. 2010; 10:1018-24.
27. Chen Y A, Chen K C, Tsai V F S, Huang Z W, Hsieh J T, Wo A M. Direct characterization of motion-dependent parameters of sperm in a microfluidic device: Proof of principle. Clin Chem. 2013; 59:493-501.
28. Xie L, Ma R, Han C, Su K, Zhang Q, Qiu T, et al. Integration of sperm motility and chemotaxis screening with a microchannel-based device. Clin Chem. 2010; 56:1270-8.
29. Yetisen A K, Akram M S, Lowe C R. Paper-based microfluidic point-of-care diagnostic devices. Lab Chip. 2013; 13:2210-51.
30. Gong M M, MacDonald B D, Nguyen T V, Van Nguyen K, Sinton D. Lab-in-a-pen: a diagnostics format familiar to patients for low-resource settings. Lab Chip. 2014; 14:957-63.
31. Gong M M, Zhang P, MacDonald B D, Sinton D. Nanoporous membranes enable concentration and transport in fully wet paper-based assays. Anal Chem. 2014; 86:8090-7.
32. Cate D M, Adkins J a, Mettakoonpitak J, Henry C S. Recent Developments in Paper-Based Microfluidic Devices. Anal Chem. 2015;
33. Coppola M A, Klotz K L, Kim K-A A, Cho H Y, Kang J, Shetty J, et al. SpermCheck Fertility, an immunodiagnostic home test that detects normozoospermia and severe oligozoospermia. Hum Reprod. 2010; 25:853-61.
34. Yu-an Chen, Zi-wei Huang, Fang-sheng Tasi, Chang-yu C C, Wo. Analysis of sperm concentration and motility in a microfluidic device. Microfluid Nanofluidics. 2011; 10:59-67.
35. Bjorndahl L, Kirkman-Brown J, Hart G, Rattle S, Barratt C L R. Development of a novel home sperm test. Hum Reprod. 2006; 21:145-9.
36. Nasr-Esfahani M H, Aboutorabi R, Esfandiari E, Mardani M. Sperm M T T viability assay: A new method for evaluation of human sperm viability. J Assist Reprod Genet. 2002; 19:477-82.
37. Gavella M, Lipovac V. NADH-dependent oxidoreductase (diaphorase) activity and isozyme pattern of sperm in infertile men. Arch Androl. 1992; 28:135-41.
38. Berridge M V., Herst P M, Tan A S. Tetrazolium dyes as tools in cell biology: New insights into their cellular reduction. Biotechnol Annu Rev. 2005; 11:127-52.
39. Matsuura K, Chen K-H H, Tsai C-H H, Li W, Asano Y, Naruse K, et al. Paper-based diagnostic devices for evaluating the quality of human sperm. Microfluid Nanofluidics. 2014; 16:857-67.

Therefore what is claimed is:

1. A device for quantifying fertility potential from a semen sample by calculating total concentration of live sperm, total concentration of live motile sperm and sperm motility in the sample as compared with reference values defined by the World health Organization, comprising:
    a transparent or semitransparent substrate layer;
    a first layer comprised of a hydrophilic porous material secured on top of the substrate layer, the first layer having first and second reaction spots spaced from each other and each reaction spot containing a colorimetric agent selected to undergo reaction with sperm such that upon reaction with sperm a color change occurs;
    a porous membrane covering said second reaction spot, said membrane having pores in a size range large enough to allow sperm to swim through the membrane and small enough to prevent the sperm in the semen sample to flow through the membrane;
    a second layer comprised of a hydrophilic porous material secured on top of the first layer, said second layer including first and second holes being located with respect to each other such that when the second layer is affixed to a top surface of the first layer said first and second holes are aligned with the first and second reaction spots; and
    wherein upon application of a first portion of a semen sample directly to said first reaction spot through said hole in said second layer a color change occurs when live sperm is present and the intensity of reacted colorimetric agent is measured using a software package to calculate total concentration of live sperm, and upon application of a second portion of the semen sample through the second hole onto the membrane any change in color indicates motile sperm is present in the second portion that traversed through the porous membrane to contact the second reaction spot and the intensity of reacted colorimetric agent located in the second reaction spot is used to calculate total concentration of live motile sperm, and the ratio of total live motile sperm concentration to total live sperm concentration is used to calculate sperm motility.

2. The device according to claim 1, including a third spot located on said second layer spaced from the first and second reactions spots, said third spot having a colorimetric agent coated thereon, said first layer not including a hole in registration with said third spot.

3. The device according to claim 1, including a buffer solution formulated to have a viscosity to simulate in vivo fluid in the female tract, said buffer solution configured to be applied to a top surface of the porous membrane prior to application of a semen sample thereto such that in operation any live sperm must traverse through the buffer solution and then through the porous membrane.

4. The device according to claim 3, including an integrated sealed buffer reservoir having a removable seal configured to be released by a user onto the top surface of the porous membrane, said buffer chamber being in flow communication with said surface of the porous membrane.

5. The device according to claim 4, including wherein the integrated sealed buffer reservoir is in flow communication with said surface of the porous membrane via a channel to the membrane from the buffer reservoir.

6. The device according to claim 1, wherein said porous membrane is hydrated, and including a separate detachable cover covering the top surface of the membrane for maintaining its moisture content while maintaining the rest of device dry.

7. The device according to claim 1, wherein the porous membrane is selected such that it is saturated with the second portion of the semen sample to facilitate flow through the porous membrane.

8. The device according to claim 1 including an analysis system and a software package, the software package configured to be programmed into an analysis system, said analysis system including a color sensor configured to sense a color of the colorimetric agents in the first and second reaction spots through a bottom surface of said transparent or semitransparent substrate layer.

9. The device according to claim 8 wherein said software package is programmed with instructions to calculate
   a total concentration of live sperm in the first portion of semen located on the first reaction spot based on an intensity of reacted colorimetric agent in said first reaction spot, and
   a total concentration of live motile sperm in the second portion of semen that traversed through said liquid buffer and said porous membrane to said second reaction spot based on an intensity of reacted colorimetric agent in said second reaction spot.

10. The device according to claim 9 wherein said software package is programmed with instructions to calculate sperm motility based on the total concentration of live sperm and total concentration motile sperm.

11. The device according to claim 8 wherein said analysis system includes a visual display, and wherein said software package is programmed with instructions to visually display said total concentration live sperm and total concentration of motile sperm, and sperm motility.

12. The device according to claim 8 wherein the analysis system is a computer system interfaced with a camera programmed with said software package, said computer system having a visual display.

13. The device according to claim 8 wherein the analysis system is a smart phone having a built-in camera and said software package is a smart phone application loaded onto said smart phone.

14. The device according to claim 1 wherein the first and second layers are made of paper based hydrophilic porous materials.

15. The device according to claim 1 wherein the first and second layers are made of polymer based hydrophilic porous material.

16. The device according to claim 1 configured for testing human sperm, and wherein the membrane has pores in a size range from about 5 to about 12 microns.

17. The device according to claim 1 wherein the membrane has pores in a size range from about 4 to about 14 microns.

18. A method for quantifying fertility potential from a semen sample by calculating total concentration of live sperm, total concentration of live motile sperm and sperm motility in the sample as compared with reference values defined by the World health Organization, comprising:
   a) applying a first portion of a semen sample onto a colorimetric agent localized on a first reaction area on a support structure;
   b) applying a second portion of the semen sample onto a second reaction area on the support structure, the second reaction area including a colorimetric agent localized on a second reaction area on the support structure and a porous membrane located on top of the colorimetric agent and a liquid buffer having sufficient viscosity to simulate in vivo fluid in the female tract located on top of the porous membrane such that motile sperm in the second portion of the semen sample must pass first through the liquid buffer and then the porous membrane to reach the colorimetric agent located on the second reaction area of the support structure, the porous membrane having pores in a size range large enough to allow sperm to swim through the membrane and small enough to prevent the sperm in the semen sample to flow through the membrane; and
   c) observing any color change in the colorimetric agents localized on the first and second reaction areas, and when color changes are present, comparing an intensity change on the first reaction area to an intensity of unreacted colorimetric agent and comparing an intensity change on the second reaction area to an intensity of unreacted colorimetric agent and, by taking a visual recording, based on these intensity changes, determining a total concentration of live sperm on the first reaction area and determining a total concentration of live motile sperm on the second reaction area, and then determining sperm motility using the ratio of total live motile sperm concentration to total live sperm concentration.

19. The method according to claim 18, wherein the intensity of unreacted colorimetric agents are the intensities of the colorimetric agents on the first and second reaction areas obtained prior to exposure to the semen sample.

20. The method according to claim 18, including a third spot located on said second layer spaced from the first and second reactions spots, said third spot having a colorimetric agent coated thereon, said first layer not including a hole in registration with said third spot such that the colorimetric agent on the third spot acts as a calibration spot giving the color of unreacted colorimetric agent against which the intensities of the colorimetric agents on the first and second reaction areas obtained after to exposure to the semen sample are compared.

21. The method according to claim 19, wherein observing any color changes localized on the first and second reaction areas includes taking a visual recording of the colorimetric agents localized on the first and second reaction areas prior to exposure to the semen sample and after exposure to the semen sample, and calculating an intensity of the colorimetric agent on each the first and second reaction areas before and after exposure, and from these intensities calculating a total concentration of live sperm in the first portion of semen located on the first reaction spot based on an intensity of reacted colorimetric agent in said first reaction spot, and a total concentration of live motile sperm in the second portion of semen that traversed through said liquid buffer and said porous membrane to said second reaction spot based on an intensity of reacted colorimetric agent in said second reaction spot.

22. The method according to claim 20, wherein observing any color changes localized on the first and second reaction areas includes taking a visual recording of the colorimetric agents localized on the first and second reaction areas and in the calibration spot, and calculating an intensity of the colorimetric agent on each the first and second reaction areas and the third spot, and from these intensities calculating a total concentration of live sperm in the first portion of semen located on the first reaction spot based on an intensity of reacted colorimetric agent in said first reaction spot, and a total concentration of live motile sperm in the second portion of semen that traversed through said liquid buffer and said porous membrane to said second reaction spot based on an intensity of reacted colorimetric agent in said second reaction spot.

23. The method according to claim 21, including visually displaying the total concentration of live sperm, the total concentration motile sperm, and sperm motility.

24. The method according to claim 18, wherein the step b) of applying a second portion of the semen sample onto a second reaction area on the support structure, is done such that any motile sperm present must flow vertically down through the liquid buffer layer and through the porous membrane to the colorimetric agent.

25. The method according to claim 18, wherein the semen sample is from a human, and wherein the membrane has pores in a size range from about 5 to about 12 microns.

26. The method according to claim 18 wherein the membrane has pores in a size range from about 4 to about 14 microns.

27. A kit comprising:
A) a sensor device including
i) a transparent or semitransparent substrate layer;
ii) a first layer comprised of a hydrophilic porous material secured on top of the substrate layer, the first layer having first and second reaction spots spaced from each other and each reaction spot containing a colorimetric agent selected to undergo reaction with sperm such that upon reaction with sperm a color change occurs;
iii) a porous membrane covering said second reaction spot, said membrane having pores in a size range large enough to allow sperm to swim through the membrane and small enough to prevent the sperm in the semen sample to flow through the membrane; and
iv) a second layer comprised of a hydrophilic porous material secured on top of the first layer, said second layer including first and second holes being located with respect to each other such that when the second layer is affixed to a top surface of the first layer said first and second holes are aligned with the first and second reaction spots;
B) optionally a buffer solution formulated to have a viscosity to simulate in vivo fluid in the female tract, said buffer solution configured to be applied to a top surface of the porous membrane prior to application of a semen sample thereto such that in operation any live sperm must traverse through the buffer solution and then through the porous membrane; and
C) wherein upon application of a first portion of a semen sample directly to said first reaction spot through said hole in said second layer a color change occurs when live sperm is present, and upon application of a second portion of the semen sample through the second hole onto the membrane any change in color indicates motile sperm is present in the second portion that traversed through the porous membrane to contact the second reaction spot.

28. The kit according to claim 27, including a third spot located on said second layer spaced from the first and second reactions spots, said third spot having a colorimetric agent coated thereon, said first layer not including a hole in registration with said third spot such that the colorimetric agent on the third spot acts as a calibration spot giving the color of unreacted colorimetric agent against which the intensities of the colorimetric agents on the first and second reaction areas obtained after to exposure to the semen sample are compared.

29. The kit according to claim 27, wherein the membrane has pores in a size range from about 5 to about 12 microns.

30. The kit according to claim 27, wherein the membrane has pores in a size range from about 4 to about 14 microns.

31. The kit according to claim 27 including a collection cup for collecting the semen from the user and a pipette for dispensing the semen from the collection cup onto the first reaction area and onto a top of the porous membrane and optionally on top of the liquid buffer layer.

* * * * *